United States Patent
Garcia Kilroy et al.

(10) Patent No.: US 10,791,301 B1
(45) Date of Patent: Sep. 29, 2020

(54) METHOD AND SYSTEM FOR SYNCHRONIZING PROCEDURE VIDEOS FOR COMPARATIVE LEARNING

(71) Applicant: Verb Surgical Inc., Mountain View, CA (US)

(72) Inventors: Pablo Garcia Kilroy, Menlo Park, CA (US); Jagadish Venkataraman, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

(21) Appl. No.: 16/440,647

(22) Filed: Jun. 13, 2019

(51) Int. Cl.
| H04N 7/169 | (2011.01) |
| G11B 27/32 | (2006.01) |
| G06K 9/00 | (2006.01) |
| G16H 70/20 | (2018.01) |

(52) U.S. Cl.
CPC ......... *H04N 7/169* (2013.01); *G06K 9/00711* (2013.01); *G11B 27/323* (2013.01); *G16H 70/20* (2018.01); *G06K 2009/00738* (2013.01)

(58) Field of Classification Search
CPC .... H04N 7/169; G16H 70/20; G06K 9/00711; G06K 2009/00738; G11B 27/323
See application file for complete search history.

(56) References Cited

U.S. PATENT DOCUMENTS

| 2010/0167250 A1* | 7/2010 | Ryan .................... G09B 23/285 434/267 |
| 2013/0218137 A1 | 8/2013 | Abovitz et al. |
| 2019/0090969 A1* | 3/2019 | Jarc ........................ A61B 34/25 |

FOREIGN PATENT DOCUMENTS

| JP | 2008058364 | 3/2008 |
| JP | 2015171437 | 10/2015 |
| KR | 10-2017-0030687 | 3/2017 |
| KR | 10-1864380 | 6/2018 |

OTHER PUBLICATIONS

International Search Report and Written Opinion for International Application No. PCT/US2019/038603, dated Mar. 16, 2020, 10 pages.

* cited by examiner

*Primary Examiner* — Michael E Teitelbaum
(74) *Attorney, Agent, or Firm* — Womble Bond Dickinson (US) LLP

(57) ABSTRACT

Embodiments described herein provide various examples of preparing two procedure videos, in particular two surgical procedure videos for comparative learning. In some embodiments, to allow comparative learning of two recorded surgical videos, each of the two recorded surgical videos is segmented into a sequence of predefined phases/steps. Next, corresponding phases/steps of the two segmented videos are individually time-synchronized in pair-wise manner so that a given phase/step of one recorded video and a corresponding phase/step of the other segmented video can have the same or substantially the same starting time and ending timing during comparative playbacks of the two recorded videos. The disclosed comparative-learning techniques can generally be applied to any type of procedure videos which can be broken down into a sequence of predefined phases/steps, and to synchronize/slave one such procedure video to another procedure video of the same type at each segmented phase/step in the sequence of predefined phases/steps.

20 Claims, 6 Drawing Sheets

METHOD AND SYSTEM FOR SYNCHRONIZING PROCEDURE VIDEOS FOR COMPARATIVE LEARNING

TECHNICAL FIELD

The present disclosure generally relates to building surgical procedure video analysis tools and, more specifically, to systems, devices and techniques for synchronizing surgical videos of a given surgical procedure so that the surgical videos can be played back automatically synchronized at a sequence of predefined phases of the surgical procedure for comparative learning.

BACKGROUND

Recorded videos of medical procedures such as surgeries contain highly valuable and rich information for medical education and training, assessing and analyzing the quality of the surgeries and skills of the surgeons, and for improving the outcomes of the surgeries and skills of the surgeons. There are many surgical procedures which involve displaying and capturing video images of the surgical procedures. For example, almost all minimally invasive procedures (MIS), such as endoscopy, laparoscopy, and arthroscopy, involve using video cameras and video images to assist the surgeons. Furthermore, the state-of-the-art robotic-assisted surgeries require intraoperative video images being captured and displayed on the monitors for the surgeons. Consequently, for many of the aforementioned surgical procedures, e.g., a gastric sleeve or cholecystectomy, a large cache of surgical videos already exist and continue to be created as a result of a large number of surgical cases performed by many different surgeons from different hospitals.

It is well-accepted that a recorded surgical procedure video can be used to assess and analyze the quality of the surgery and skills of the surgeon. However, by merely watching a surgeon performing certain surgical tasks recorded on a surgical procedure video, it can be quite difficult to objectively assess the surgeon's performance because there is no clear reference or metric for gauging whether the surgeon did a good job or not in each surgical task. As an improvement to the above technique, a comparative-learning technique involves an expert simultaneously watching two surgical videos performed by two surgeons, visually comparing the techniques of the two surgeons, and more objectively assigning scores for the surgical tasks performed by the two surgeons. As a further improvement to the above techniques, another comparative-learning technique involves two recorded procedure videos playing side by side: the first video being a reference video performed by an expert of the surgical procedure; whereas the second video being an evaluation video performed by a second surgeon. Again, an expert is tasked to simultaneously watch the two side-by-side videos, compare the techniques of the second surgeon against those of the expert, and subsequently assign a skill score for the second surgeon based on the direct comparison of the second surgeon in the second video to the expert in the first video.

SUMMARY

This patent disclosure provides various embodiments of preparing two procedure videos, in particular two surgical procedure videos for comparative learning. In some embodiments, to allow comparative learning of two recorded surgical videos, each of the two recorded surgical videos is segmented into a sequence of predefined phases/steps. Next, corresponding phases/steps of the two segmented videos are individually time-synchronized in pair-wise manner so that a given phase/step of one segmented video and a corresponding phase/step of the other segmented video can have the same or substantially the same starting time and ending timing during comparative playbacks of the two recorded videos, e.g., on two side-by-side monitors.

In some embodiments, the proposed comparative learning techniques also include comparative playing and viewing of a recorded video and a live video feed side by side. To do so, the recorded video may be segmented into a sequence of predefined steps prior to the playback (i.e., processed offline). Next, during a live practice session, the proposed techniques provide a mechanism to identify the predefined steps in the live video feed in real-time and subsequently slave the playback of a predefined step in the recorded video to a corresponding predefined step identified in the live video feed. In this manner, the recorded video can pause, restart, and follow the speed of the live video feed depicting a person replicating the actions in the recorded video through the sequence of predefined steps.

In one aspect, a process for synchronizing two surgical procedure videos is disclosed. This process can begin by receiving a first surgical video of a surgical procedure and a second surgical video of the same surgical procedure, wherein the surgical procedure includes a sequence of predefined phases. The process next performs a phase segmentation operation on each of the first and second surgical videos to segment the first and second surgical videos into a first set and a second set of video segments corresponding to the sequence of predefined phases. Next, the process synchronizes each video segment in the first set of video segments corresponding to a predefined phase in the sequence of predefined phases to a corresponding video segment in the second set of video segments corresponding to the same predefined phase. The process subsequently outputs the first and second surgical videos including the first and second sets of synchronized video segments to a display system for a comparative viewing.

In some embodiments, the process segments the first or the second surgical video into the first or the second set of video segments by: for each phase in the sequence of predefined phases, identifying a first phase boundary in the first or the second surgical video representing the beginning of the phase in the first or the second surgical video; identifying a second phase boundary in the first or the second surgical video representing the ending of the phase in the first or the second surgical video; and outputting a video segment between the first phase boundary and the second phase boundary of the first or the second surgical video as the video segment corresponding to the given phase. Note that each video segment in the first or the second set of video segments includes a corresponding set of video frames.

In some embodiments, the process identifies the first or the second phase boundary in the first or the second surgical video by using a machine-learning engine to detect a surgical event in the first or the second surgical video indicative of the beginning or ending of the corresponding phase in the surgical procedure.

In some embodiments, the process synchronizes each video segment in the first set of video segments of the first surgical video to a corresponding video segment in the second set of video segments of the second surgical video by: time-aligning the first phase boundary of the video segment of the first surgical video to the first phase boundary of the corresponding video segment of the second surgical video; and determining a first playback speed for the video segment and a second playback speed for the corresponding video segment such that a first playback time of the video segment using the first playback speed is equal to or substantially equal to a second playback time of the corresponding video segment using the second playback speed. In this manner, the process allows the second phase boundary of the video segment of the first surgical video to be time-aligned to the second phase boundary of the corresponding video segment of the second surgical video.

In some embodiments, the process synchronizes a given video segment in the first set of video segments of the first surgical video to a corresponding video segment in the second set of video segments of the second surgical video by: determining a first number of video frames contained in the given video segment; determining a second number of video frames contained in the corresponding video segment; and determining a first frame rate for playing back the given video segment and a second frame rate for playing back the corresponding video segment based on the first number and the second number of video frames, so that a first playback time of the given video segment using the first frame rate is equal to or substantially equal to a second playback time of the corresponding video segment using the second frame rate.

In some embodiments, the first frame rate is a constant frame rate for all video segments of the first surgical video, and wherein the second frame rate is computed based on the constant frame rate and the first number and the second number of video frames.

In some embodiments, the first surgical video is a reference video, and the process synchronizes a given video segment in the first set of video segments to a corresponding video segment in the second set of video segments by: assigning a constant playback speed for all video segments in the first set of video segments; and for each video segment in the second set of video segments, assigning an adjustable playback speed based on a playback time of the corresponding video segment in the first set of video segments when using the constant playback speed. More specifically, the adjustable playback speed is configured to speed up or slow down the playback of a video segment in the second set of video segments so that the playback time of each video segment in the first set of video segments when using the constant playback speed is equal to or substantially equal to the playback time of each video segment in the first set of video segments using the adjustable playback speed.

In some embodiments, the process performs a comparative viewing of the first and second surgical videos by: outputting the first surgical video to a first monitor and the second surgical video to a second monitor which is positioned next to the first monitor; and simultaneously starting a playback of the first surgical video on the first monitor and a playback of the second surgical video on the second monitor. Note that playing the first surgical video and the second surgical video based on the two sets of synchronized video segments automatically synchronizes the playback of each video segment in the first set of video segments to the playback of a corresponding video segment in the second set of video segments.

In some embodiments, the playback of the first surgical video on the first monitor ends at the same time or substantially the same time as the playback of the second surgical video on the second monitor ends.

In some embodiments, the process performs a comparative viewing of the first and second surgical videos by: creating a split-screen video by combining the first and second surgical videos, wherein the corresponding video segments in the first and second surgical videos are time-aligned at the corresponding phase boundaries in the split-screen video; and playing back the split-screen video on a monitor so that the first and second surgical videos are played side-by-side and time-aligned to each other in each of the sequence of predefined phases.

In another aspect, a system for synchronizing two surgical procedure videos is disclosed. This system can include: one or more processors; a memory coupled to the one or more processors; a segmentation module configured to segment a first surgical video and a second surgical video of a same surgical procedure into a first set of video segments and a second set of video segments, respectively, based on a sequence of predefined phases for the surgical procedure; a synchronization module configured to synchronize a video segment in the first set of video segments corresponding to a predefined phase in the sequence of predefined phases to a corresponding video segment in the second set of video segments corresponding to the same predefined phase; and an output module configured to output the synchronized video segments to a display system for a comparative viewing.

In some embodiments, the segmentation module is configured to segment the first surgical video or the second surgical video by: for each phase in the sequence of predefined phases, identifying a first phase boundary in the first or the second surgical video representing the beginning of the phase in the first or the second surgical video; identifying a second phase boundary in the first or the second surgical video representing the ending of the phase in the first or the second surgical video; and outputting a video segment between the first phase boundary and the second phase boundary of the first or the second surgical video as the video segment corresponding to the given phase. Note that each video segment in the first or the second set of video segments includes a corresponding set of video frames.

In some embodiments, the segmentation module is further configured to identify the first or the second phase boundary in the first or the second surgical video by using a machine-learning engine to detect a surgical event in the first or the second surgical video indicative of the beginning or ending of the corresponding phase in the surgical procedure.

In some embodiments, the synchronization module is configured to synchronize the video segment in the first set of video segments to the corresponding video segment in the second set of video segments by: time-aligning the first phase boundary of the video segment of the first surgical video to the first phase boundary of the corresponding video segment of the second surgical video; and determining a first playback speed for the video segment and a second playback speed for the corresponding video segment such that a first playback time of the video segment using the first playback speed is equal to or substantially equal to a second playback time of the corresponding video segment using the second playback speed. In this manner, the synchronization module enables the second phase boundary of the video segment of the first surgical video to be time-aligned to the second phase boundary of the corresponding video segment of the second surgical video.

In some embodiments, the synchronization module is further configured to synchronize the video segment in the first set of video segments to the corresponding video segment in the second set of video segments by: determining a first number of video frames contained in the given video segment; determining a second number of video frames contained in the corresponding video segment; and determining a first frame rate for playing back the given video segment and a second frame rate for playing back the corresponding video segment based on the first number and the second number of video frames, so that a first playback time of the given video segment using the first frame rate is equal to or substantially equal to a second playback time of the corresponding video segment using the second frame rate.

In some embodiments, the first frame rate is a constant frame rate for all video segments of the first surgical video, and wherein the second frame rate is computed based on the constant frame rate, and the first number and the second number of video frames.

In some embodiments, the first surgical video is a reference video, and the phase synchronization module is further configured to synchronize a given video segment in the first set of video segments of the first surgical video to a corresponding video segment in the second set of video segments of the second surgical video by: assigning a constant playback speed for all video segments in the first set of video segments; and for each video segment in the second set of video segments, assigning an adjustable playback speed based on a playback time of the corresponding video segment in the first set of video segments when using the constant playback speed. More specifically, the phase synchronization module configures the adjustable playback speed to speed up or slow down the playback of a video segment in the second set of video segments so that the playback time of each video segment in the first set of video segments when using the constant playback speed is equal to or substantially equal to the playback time of each video segment in the first set of video segments using the adjustable playback speed.

In some embodiments, the output module is further configured to: output the video segment in the first set of video segments to a first monitor and the corresponding video segment in the second set of video segments to a second monitor which is positioned next to the first monitor; and simultaneously start a playback of the video segment of the first surgical video on the first monitor and a playback of the corresponding video segment of the second surgical video on the second monitor. By playing the first surgical video and the second surgical video based on the two synchronized video segments, the system automatically synchronizes the playback of the video segment of the first surgical video to the playback of the corresponding video segment of the second surgical video.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1A:
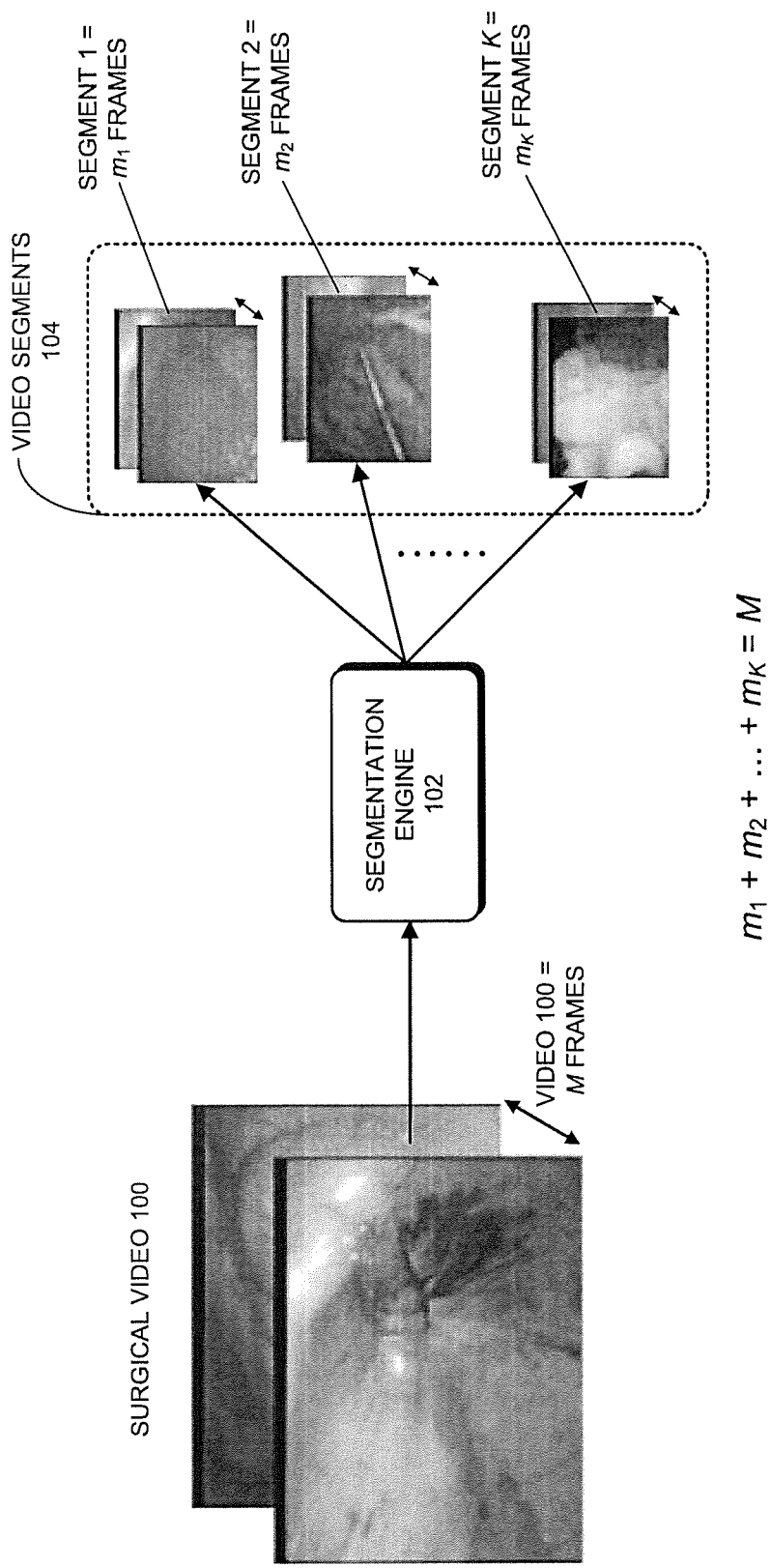
FIG. 1A shows an exemplary surgical video segmentation process for segmenting a first surgical video of a surgical procedure comprising M video frames into a set of K video segments in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

In this patent disclosure, various embodiments of preparing two procedure videos, in particular two surgical procedure videos for comparative learning are disclosed. In some embodiments, to allow comparative learning of two recorded surgical videos, each of the two recorded surgical videos is segmented into a sequence of predefined phases/steps. Next, corresponding phases/steps of the two segmented videos are individually time-synchronized in pairwise manner so that a given phase/step of one segmented video and a corresponding phase/step of the other segmented video can have the same or substantially the same starting time and ending timing during comparative playbacks of the two recorded videos, e.g., on two side-by-side monitors. In some embodiments, the proposed comparative learning techniques also include comparative playing and viewing of a recorded video and a live video feed side by side. To do so, the recorded video may be segmented into a sequence of predefined steps prior to the playback (i.e., processed offline). Next, during a live practice session, the proposed techniques provide a mechanism to identify the predefined steps in the live video feed in real-time and subsequently slave the playback of a predefined step in the recorded video to a corresponding predefined step identified in the live video feed. In this manner, the recorded video can pause, restart, and follow the speed of the live video feed through the sequence of predefined steps.

Note that surgical procedure videos (or "surgical videos" hereinafter) represent a class of procedure videos wherein each video can be broken down to a sequence of predefined surgical steps or phases, wherein each phase in the sequence of predefined phases represents a particular stage of the surgical procedure that serves a unique and distinguishable purpose in the entire surgical procedure. In some embodiments, a given surgical video described herein is recorded specifically for the intraoperative period of the surgical procedure. The predefined sequence of phases can be initially established based on a well-recognized and/or standardized operation procedure retrievable from a surgical information management system (IMS) which identifies key phases within a given surgical procedure. Using the sequence of predefined phases and a surgical phase segmentation engine (or "phase segmentation engine" hereinafter), a surgical video, which can be a rather long video, can be segmented into a set of shorter video segments, and each video segment corresponds to a particular phase of the surgical procedure which is distinguishable from other video segments corresponding to other phases of the surgical procedure. In some embodiments, the phase segmentation engine can further break down a given predefined phase into a sequence of subphases, wherein each of the subphases corresponds to single task among a sequence of tasks which are performed within the given predefined phase. In such embodiments, it is possible to further divide a phase segment of the surgical video into even smaller segments corresponding to the individual tasks within the given phase. More detailed operation of the phase segmentation engine has been described in a related patent application having Ser. No. 15/987,782, and filing date May 23, 2018, the content of which is incorporated by reference herein.

Comparative Learning Between Two Recorded Videos

Note that two recorded surgical videos corresponding to the same surgical procedure, such as the gastric sleeve procedure or cholecystectomy typically contain the same sequence of predefined phases or stages. For example, the two recorded videos can be generated from the same surgeon performing the same surgical procedure on two different patients, or from two different surgeons performing the same surgical procedure on two different patients. In each of the above scenarios, it can be beneficial to compare the performances of the same surgeon in two different surgeries or the two different surgeons doing the same procedure by comparatively playing and viewing the two recorded videos, e.g., in a two-monitor side-by-side setup. Also note that in each of the above scenarios, while the two recorded videos may be composed of the same sequence of predefined phases, a pair of corresponding video segments in the two videos may differ in lengths and the numbers of video frames. Hence, if the two recorded videos are not time-synchronized at the individual phases, the comparative viewing would require the observer to manually pause (e.g., when the first video completes phase 1 before the second video) and restart (e.g., when the second video completes phase 1 sometime later) one of the two videos, and go back and forth between the two videos in order to synchronize the playbacks of the two videos in corresponding phases.

To enable automated comparative playing and viewing (also referred to as "comparative learning" in this patent disclosure) of two recorded videos of a given surgical procedure, some embodiments of this patent disclosure first apply a corresponding phase segmentation engine to the two recorded videos to break down/segment each of the two videos into a sequence of predefined phases. For example, a first recorded video $V_1$ may be segmented into a set of N video segments corresponding to a sequence of N predefined phases (e.g., N=6 or 8) for the given surgical procedure, and the second recorded video $V_2$ can also be segmented into a set of N video segments corresponding to the same sequence of N predefined phases (e.g., N=6 or 8) for the same surgical procedure. Moreover, for each identified surgical phase in $V_1$ or $V_2$, the two phase boundaries, i.e., the beginning timestamp and the ending timestamp of the corresponding video segment can also be determined by the phase segmentation engine. Note that while the N predefined phases in each of the two recorded videos are identical to each other, the durations of and number of frames within a given phase in the two recorded videos can be different. Next, during the playbacks of the two videos $V_1$ and $V_2$, each video segment in the set of N video segments of $V_1$ can be played time-synchronized with the playback of the corresponding video segment of $V_2$. For example, depending on the number of frames in each of the two corresponding video segments of the two videos $V_1$ and $V_2$, the frame rate of the video player can be adjusted for either video such that each corresponding video segment starts and ends at the same or substantially the same time for the playbacks of the two videos.

Note that while the disclosed comparative-learning techniques (e.g., by way of side-by-side playback and viewing) are generally described above and further below based on segmenting a surgical video into a sequence of predefined phases, the segmentation of the surgical video can include finer granularities than just a set of high-level phases. For example, each of the two recorded videos can be first segmented into a set video segments corresponding to a set of predefined high-level surgical phases. Next, a subset of video segments corresponding to one or more phases in the set of high-level surgical phases can be further segmented into a set of surgical subphases/tasks. In other words, each of the subset of video segments can be broken down into a set of even shorter video segments of individual surgical tasks. At the end of the video segmentation, the two recorded videos can be segmented into a combined sequence of predefined phases and tasks. In other words, for the first video having an identified phase or task, there is a corresponding phase or task identified in the second video, no matter how long or how short that phase or task is. For the simplicity of discussion, we describe various embodiments of synchronizing the playbacks of two recorded videos in the scope of the sequence of predetermined phases. However, the disclosed techniques below between the two recorded videos can be equally applicable to synchronizing video segments of finer granularities, such as subphases, steps, and tasks without departing from the scope of this patent disclosure.

In some embodiments, the total procedure times associated with the two recorded videos can be the same even if some corresponding video segments/phases of the two videos have different durations/lengths. For example, if video $V_1$ has a given phase which is two minutes longer than the corresponding phase in video $V_2$, but also has another phase which is two minutes shorter than the corresponding phase in $V_2$, then $V_1$ and $V_2$ can still have the same total video length. In this example, if the two videos start comparative playbacks at the same time, the two playbacks would also end at the same or substantially the same time. However, for the first video segment corresponding to phase $P_1$ of the sequence of predefined phases, the playback of phase $P_1$ in $V_1$ may end at a different time than the end of the playback of the corresponding phase $P_1$ in $V_2$, i.e., the playbacks of phase $P_1$ are not automatically time-synchronized (or "time-synced") between the two videos $V_1$ and $V_2$.

For comparative viewing and learning, it is beneficial to play back the two recorded videos in such a manner that every video segment/phase in the first video is time-synchronized to a corresponding video segment/phase in the second video. In some embodiments, the synchronized playbacks of the two videos can be achieved by playing the set of video segments at various speeds such that the corresponding video segments in the two videos are always synchronized at the corresponding video-segment boundaries (also referred to as the "phase boundaries" for the corresponding phase). More specifically, after performing phase segmentation on the two videos, the lengths and phase boundaries of each video segment of the two videos can be extracted. Next, synchronizing the playbacks of the two videos simply requires syncing-up corresponding video segments at the corresponding phase boundaries. For example, assuming a given video segment/phase in $V_1$ and the corresponding video segment/phase in $V_2$ start to play at the same time (i.e., the first phase boundaries of the given video segment/phase in the two videos have been time-aligned), then synchronizing the given video segment/phase in the two videos requires that the playbacks of the given video segment/phase in the two videos also end at the same time (i.e., the second phase boundaries of the given video segment/phase in the two videos are also time-aligned).

More specifically, if a given video segment/phase in $V_1$ and the corresponding video segment/phase in $V_2$ have different lengths/durations, then the alignment of the second phase boundary can be achieved by: (1) increasing the playback speed of the longer video segment/phase; or (2) decreasing the playback speed of the shorter video segment/phase. For example, if video segment $s_1$ in $V_1$ is 2× longer than the corresponding video segment $s_1$ in $V_2$, then slowing down the playback of video segment $s_1$ in $V_2$ by 2× will result in the playbacks of $s_1$ in the two videos to end at the same time. As another example, if video segment $s_3$ in $V_1$ is 1.5× shorter than the corresponding video segment $s_3$ in $V_2$, then speeding up the playback of video segment $s_3$ in $V_2$ by 1.5× would again result in the playbacks of video segment $s_3$ in the two videos to end at the same time. The above playback synchronization technique to align the phase boundaries of a given video segment/phase can be repeated for each and every video segment/phase of the sequence of predefined phases, thereby achieving full time-synchronizing between the two videos for all individual video segments/phases and the overall procedures. Note that when the full time-synchronizing is achieved during the comparative playing of the two videos, a viewer of the comparative playing will always be watching the same video segment/phase of the surgical procedure in the two videos at any given point of time.

In some embodiments, synchronizing the playbacks of the two segmented videos can be achieved by always playing the video segments at a slower speed. More specifically, for each of the video segments/phases, one of the two videos having the longer duration is always used as the reference video and played at a regular/constant speed, whereas the alignment of the video segment/phase is achieved by using a slower playback speed for the corresponding video segment/phase in the other video. Alternatively, synchronizing the playbacks of the two segmented videos can be achieved by always playing the video segments at a faster speed. More specifically, for each of the video segments/phases, one of the two videos having the shorter duration is always used as the reference video and played at a regular/constant speed, whereas the alignment of the video segment/phase is achieved by using a faster playback speed for the corresponding video segment/phase in the other video.

In some other embodiments, synchronizing the playbacks of the two segmented videos can be achieved by always having one video as the reference video and played at a regular speed, and then adjusting the playback speed of the other video for each of the set video segments/phases by speeding up or slowing down the playback based on the corresponding video segment/phase in the reference video to sync-up the different video segments/phases. In some embodiments, if the two videos for comparative learning include an expert/instructional/training video and a non-expert/evaluation/trainee video, then the expert/instructional/training video can be made as the reference video which would be played at its regular speed, while the non-expert/evaluation/trainee video would be played at varying speeds for each of the set of video segments/phases to sync-up with the corresponding video segment/phase in the expert/instructional/training video. Note that which of the above techniques to choose to achieve the phase-boundary alignment would often depend on the particular application associated with the video comparison.

Note that because each recorded video is composed of a set of video frames which naturally represents a time sequence, segmenting a recorded video into video segments essential divides the set of frames into subsets of frames, wherein each video segment is composed of a subset of the set of frames. FIG. 1A shows an exemplary surgical video segmentation process for segmenting a first surgical video 100 of a surgical procedure comprising M video frames into a set of K video segments in accordance with some embodiments described herein. As can be seen in FIG. 1A, surgical video 100, which is composed of M frames, is fed into a phase segmentation engine 102. Phase segmentation engine 102 is configured to segment surgical video 100 into a set of video segments 104, namely Segment 1, Segment 2, . . . , Segment K corresponding to a sequence of K predefined surgical phases. Hence, segmentation engine 102 partitions surgical video 100, which can be a rather long video, into a set of shorter video segments, and each video segment corresponds to a particular predefined phase of the surgical procedure which is distinguishable from other video segments corresponding to other predefined phases of the surgical procedure. In particular, after video segmentation, the generated set of video segments 104 (i.e., Segment 1, Segment 2, . . . , Segment K) is corresponding of a set of frames ($m_1, m_2, \ldots, m_K$). For example, Segment i of video 100 is composed of $m_i$ video frames, wherein i is any number from 1 to K. As such, $m_1+m_2+\ldots+m_K=M$. In some embodiments, video 100 is an instructional video or training video prepared by an expert of the surgical procedure.

Note that the outputs form segmentation engine 102 can also include the two phase boundaries for each video segment of the set of video segments 104 and the corresponding phase, wherein each of the two phase boundaries marks the beginning or ending of the corresponding phase. Each of the two phase boundaries can be represented by either the corresponding timestamp of the phase boundary or by the corresponding frame number of the phase boundary. Hence, the duration of a given video segment i can be computed as the difference between the two timestamps of the two phase boundaries, which is proportional to the number of frames $m_i$ (i=1, 2, . . . , K) within the video segment. In some embodiments, however, segmentation engine 102 does not directly generate the phase boundaries. Instead, a phase synchronization engine further down the processing pipeline can be used to extract the phase boundaries from the set of video segments 104.

In some embodiments, identifying a phase boundary for a corresponding phase includes using a computer vision or a machine-learning-based video image processing technique to detect the occurrence of a landmark surgical event in the surgical video indicative of the beginning or ending of the corresponding phase in the surgical procedure. For example, such a landmark event can include the appearances of particular surgical tools, the appearances of particular anatomies, and a combination of the above. Note that the second or ending phase boundary of a given phase can also be the first or beginning phase boundary of the subsequent phase in the sequence of predefined phases.

Figure 1B:
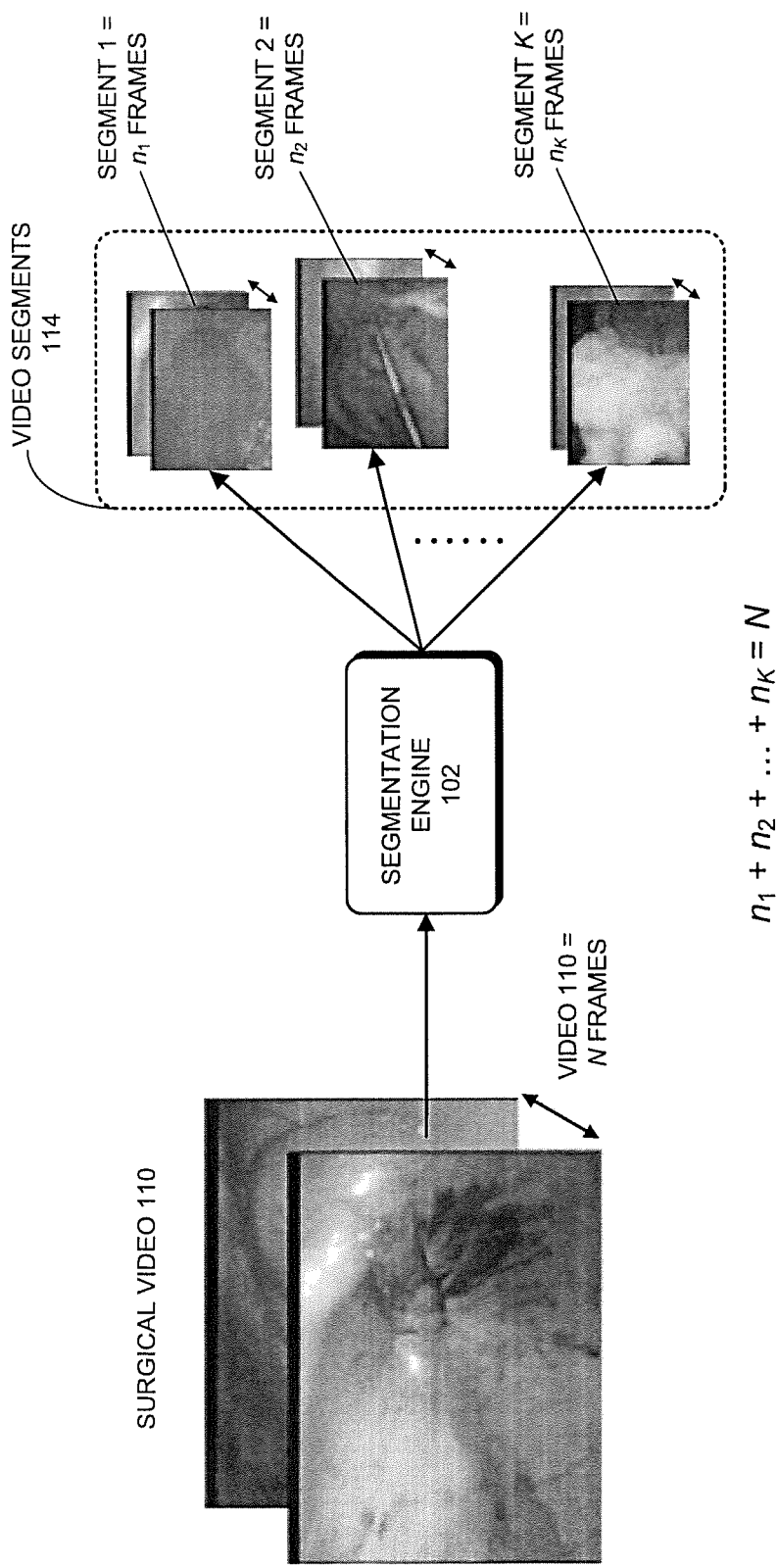
FIG. 1B shows an exemplary surgical video segmentation process for segmenting a second surgical video of the same surgical procedure comprising N video frames into a set of K segments in accordance with some embodiments described herein.

Similarly, FIG. 1B shows an exemplary surgical video segmentation process for segmenting a second surgical video 110 of the same surgical procedure comprising N video frames into a set of K segments in accordance with some embodiments described herein. As can be seen in FIG. 1B, surgical video 110, which is composed of N frames, is fed into the same phase segmentation engine 102 as in FIG. 1A. In some embodiment, surgical video 110 depicts the same surgical procedure as surgical video 100 and therefore includes the same sequence of predefined phases as surgical video 100. Hence, phase segmentation engine 102 is configured to segment surgical video 110 into a set of video segments 114, namely Segment 1, Segment 2, . . . , Segment K corresponding to the same sequence of K predefined surgical phases as in FIG. 1A. Note that after segmenting both videos 100 and 110, a Segment k (k=1, 2, . . . , K) in the set of video segments 104 and an identically-indexed Segment k (k=1, 2, . . . , K) in the set of video segments 114 correspond to the same predefined surgical phase in the same surgical procedure.

Hence, segmentation engine 102 partitions surgical video 110 into a set of shorter video segments, and each video segment corresponds to a particular predefined phase of the surgical procedure which is distinguishable from other video segments corresponding to other predefined phases of the surgical procedure. In particular, after video segmentation, the generated set of video segments 104 (i.e., Segment 1, Segment 2, . . . , Segment K) is corresponding of a set of frames $(n_1, n_2, \ldots, n_K)$. For example, Segment j of video 110 is composed of $n_j$ video frames, wherein j is any number from 1 to K. As such, $n_1+n_2+ \ldots +n_K=N$. In some embodiments, video 110 is a trainee video or a video prepared by someone who is less than an expert in the surgical procedure.

Similarly, the outputs form segmentation engine 102 can also include the two phase boundaries for each video segment of the set of video segments 114 and the corresponding phase, wherein each of the two phase boundaries marks the beginning or ending of the corresponding phase. Each of the two phase boundaries can be represented by either the corresponding timestamp of the phase boundary or by the corresponding frame number of the phase boundary. Hence, the duration of a given video segment j can be computed as the difference between the timestamps of two phase boundaries, which is proportional to the number of frames $n_j$ (j=1, 2, . . . , K) within the video segment. In some embodiments, however, segmentation engine 102 does not directly generate the phase boundaries. Instead, a phase synchronization engine further down the processing pipeline can be used to extract the phase boundaries from the set of video segments 114.

Figure 2:
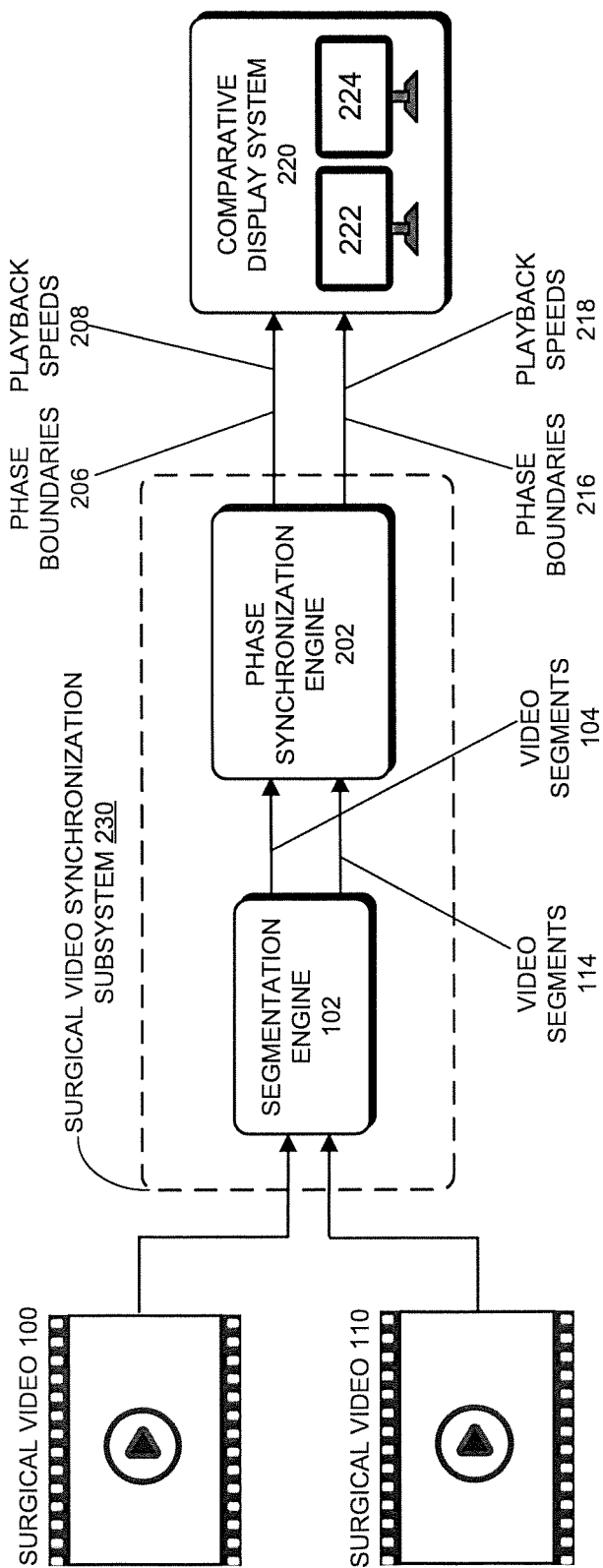
FIG. 2 shows an exemplary surgical video comparative-learning system for time-synchronizing two recorded surgical videos of the same surgical procedure and playing back the two time-synchronized surgical videos for comparative-learning in accordance with some embodiments described herein.

FIG. 2 shows an exemplary surgical video comparative-learning system 200 for time-synchronizing two recorded surgical videos 100 and 110 of the same surgical procedure and playing back the two time-synchronized surgical videos for comparative-learning in accordance with some embodiments described herein. Note that comparative-learning system 200 includes the above-described phase segmentation engine 102 in FIGS. 1A and 1B, a phase synchronization engine 202, and a comparative display system 220, which are coupled to each other in the order shown.

As can be seen in FIG. 2, phase segmentation engine 102 receives surgical videos 100 and 110 and segments each of the videos into the corresponding sets of video segments 104 and 114. Various embodiments of using phase segmentation engine 102 to segment surgical videos 100 and 110 into the corresponding sets of video segments 104 and 114 have been described above in conjunction with FIGS. 1A and 1B. In some embodiments, phase segmentation engine 102 can process surgical videos 100 and 110 in parallel or sequentially. If segmentation engine 102 processes surgical videos 100 and 110 sequentially, segmentation engine 102 can process surgical videos 100 and 110 in either order.

In some embodiments, phase synchronization engine 202 is used to time-synchronize each video segment 104 of video 100 corresponding to a given surgical phase to a corresponding video segment 114 of video 110 corresponding to the same surgical phase. More specifically, phase synchronization engine 202 can be configured to determine a first playback speed for each video segment k (k=1, 2, . . . , K) of video 100 and a second playback speed for a corresponding video segment k of video 110, so that the two video segments have the same or substantially the same playback time. In this manner, if the two video segments start playing at the same or substantially the same time, they will also reach the end of the playbacks at the same or substantially the same time.

Note that phase segmentation engine 102 and phase synchronization engine 202 combined forms a surgical video synchronization subsystem 230 for time-synchronizing two input surgical videos 100 and 110 of the same surgical procedure in preparation for comparative viewing. Note that the disclosed surgical video synchronization subsystem 230 can be a standalone system which can be used to pre-process surgical videos of the same surgical procedure and generate time-synchronization outputs (e.g., including the computed playback speeds) for use by a separate display system, such as a comparative display system 220 to perform a comparative-learning session.

As described-above, time-synchronizing two corresponding video segments k can be achieved by synchronizing/aligning the two video segments at the two corresponding phase boundaries. Hence, in some embodiments, phase synchronization engine 202 is configured to extract the two phase boundaries from video segment k of video 100 and the two phase boundaries from corresponding video segment k of video 110, and determine the durations of the two video segments from these phase boundaries. Note that the duration of a given video segment can be measured based on the time difference between the two phase boundaries and/or the number of frames in the given video segment. Because the two computed durations can be different from each other, even if the first phase boundaries of the two video segments k have been time-aligned, the second phase boundaries of the two video segments k are not automatically aligned to each other.

In some embodiments, phase synchronization engine 202 is configured to compute playback speeds for the two video segments k based on the determined durations, so that during a comparative playback, if the first phase boundaries of the two video segments k have been time-aligned, i.e., having the same or substantially the same starting time, the second phase boundaries of the two video segments k are also time-aligned, i.e., having the same or substantially the same completion time. Because each of the two video segments k is composed of a set of video frames, the playback speed for a given video segment can be measured based on a frame rate, wherein the frame rates of the two video segments k can be determined based on the number of frames in the corresponding video segments.

In a particular embodiment, assuming that the first video 100 is used as the reference video which is played at an original frame rate R, and also assuming the first phase boundaries of the two video segments k have been time-aligned, then phase synchronization engine 202 can determine the frame rate for video segment k of video 110 based on the following expression:

$$R \times (n_k/m_k),$$

wherein $m_k$ and $n_k$ are the numbers of frames in the two video segments k of videos 100 and 110, respectively. More specifically, assuming the two videos 100 and 110 start to play at the same time, then the time-synchronization for the first video segments (i.e., segment 1) in the two videos can be achieved by playing video 110 at the adjusted frame rate of $R \times (n_1/m_1)$; the time-synchronization for the second video segments (i.e., segment 2) in the two videos can be achieved by playing video 110 at the adjusted frame rate $R \times (n_2/m_2)$; and so on until the last video segments K (i.e., segment K) wherein the time-synchronization can be achieved by playing video segment K in video 110 at the adjusted frame rate $R \times (n_K/m_K)$. In this manner, the phase boundaries of every video segment/phase in the two videos 100 and 110 can always maintain time-alignment during a comparative viewing session, and the playbacks can also complete at the same or substantially the same time. Note that while we discussion the time synchronization in the scope of two surgical videos, the same concept of aligning phase boundaries during video playbacks can easily be extended to aligning multiple (i.e., two or more) surgical videos of a given surgical procedure to the same reference video of the same surgical procedure.

Hence, to time-synchronize the two input videos 100 and 110, phase synchronization engine 202 of video synchronization subsystem 230 is configured to generate a set of phase boundaries 206 for video 100 and a corresponding set of phase boundaries 216 for video 110, respectively; and also generate a set of playback speeds 208 for video 100 and a corresponding set of playback speeds 218 for video 110, respectively, wherein each playback speed can be measured in terms of a frame rate. In the above example, the set of playback speeds 208 for video 100 is a constant frame rate R; whereas the set of playback speeds 218 for video 110 is computed based on the expression $R \times (n_k/m_k)$ (k=1, 2, ..., K).

Next, the outputs from phase synchronization engine 202 can be received by comparative display system 220 configured to perform a comparative learning session for surgical videos 100 and 110. For example, display system 220 can include two side-by-side monitors 222 and 224, with video 100 playing on the first monitor 222 on the left, and with video 110 playing on the second monitor 224 on the right. A video processing module of display system 220 can control the comparative playbacks of the two videos based on the set of playback speeds 208 and the set of playback speeds 218 to ensure that the corresponding video segments/phases in the two surgical videos always aligned at the corresponding phase boundaries.

In some embodiments, comparative display system 220 can be configured to use the outputs from phase synchronization engine 202 to create a composite video by combining surgical videos 100 and 110 into a single split-screen video, with video 100 displayed on one half of the split-screen video and video 110 displayed on the other half of the split screen video. Moreover, when combining the two videos, the corresponding video segments in the split-screen video are time-aligned at the corresponding phase boundaries. Next, during a comparative view session, comparative display system 220 plays back the combined video on a single monitor, wherein the two halves of the split-screen video are always time-aligned at the corresponding phases and phase boundaries.

Figure 3:
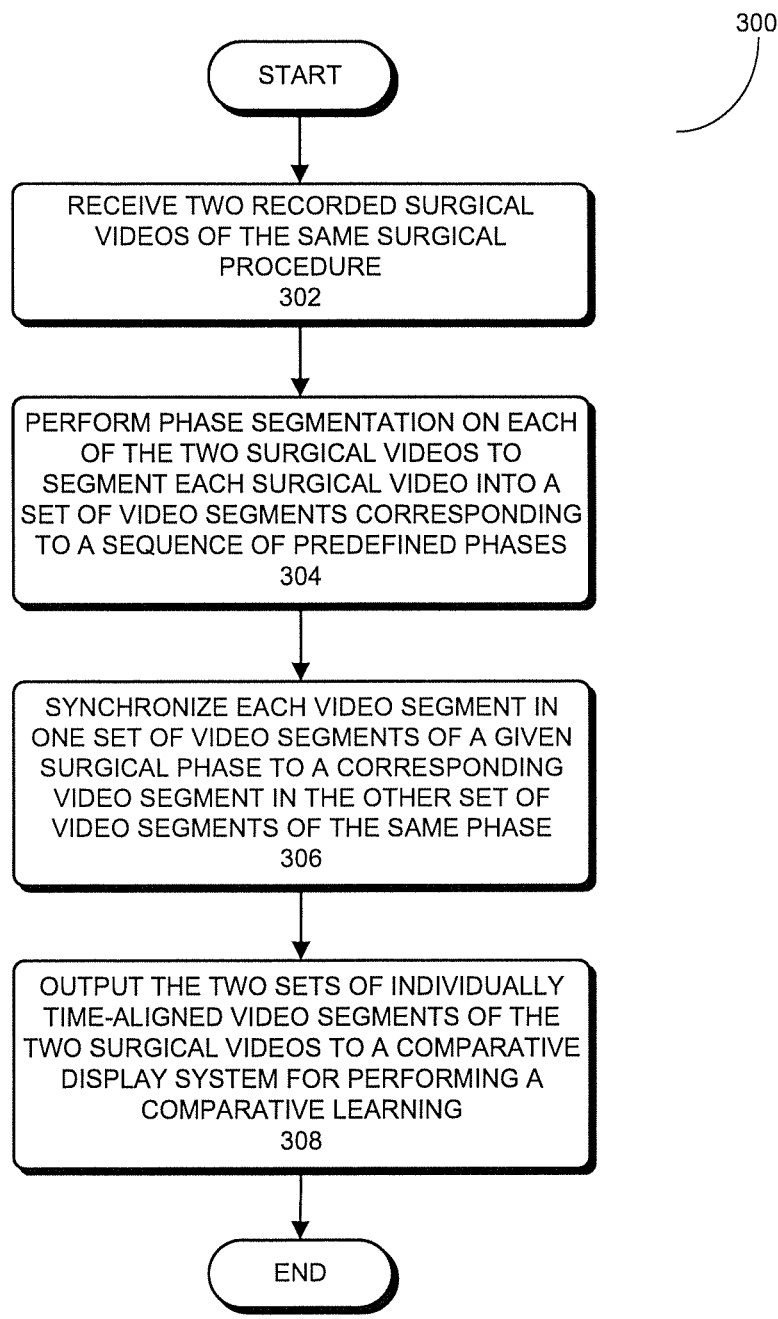
FIG. 3 presents a flowchart illustrating an exemplary process for time-synchronizing two surgical videos of the same surgical procedure for comparative learning in accordance with some embodiments described herein.

FIG. 3 presents a flowchart illustrating an exemplary process 300 for time-synchronizing two surgical videos of the same surgical procedure for comparative learning in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

As can be seen in FIG. 3, process 300 begins by receiving two recorded surgical videos of the same surgical procedure (step 302). In some embodiments, one of the two surgical videos is an instructional/training video of the surgical procedure performed by an expert of the surgical procedure, whereas the other surgical video is performed by a trainee of the surgical procedure. In other embodiments, the two recorded videos can be generated from the same surgeon performing the same surgical procedure on two different patients, or from two different surgeons performing the same surgical procedure on two different patients. Next, process 300 performs phase segmentation on each of the two surgical videos to segment each surgical video into a set of video segments corresponding to a sequence of predefined phases of the surgical procedure (step 304). For example, process 300 can use the above-described phase segmentation engine 102 to perform the phase segmentation operations. Note that because the two surgical videos are recorded videos, the phase segmentation operations can be performed offline.

Note that while each of the two segmented videos is composed of a set of video segments corresponding to the same sequence of predefined phases, a pair of corresponding video segments in the two videos (e.g., Segment 1 in the first video and Segment 1 in the second video) may differ in lengths and the numbers of video frames. In some embodiments, a given video segment in the set of video segments of one video corresponding to a given predefined phase can be further segmented into a sequence of predefined subphases, wherein each of the subphases corresponds to single task among a sequence of tasks which are performed within the given predefined phase. Similarly, a given video segment in the set of video segments of the other video corresponding to the same predefined phase can also be segmented into the sequence of predefined subphases, Next, process 300 synchronizes each video segment in one set of video segments corresponding to a given surgical phase to a corresponding video segment in the other set of video segments corresponding to the same surgical phase (step 306). For example, process 300 can determine a first playback speed for a video segment and a second playback speed for a corresponding video segment so that the two video segments can have the same or substantially the same playback time. In this manner, if the two video segments are time-aligned at the first corresponding phase boundaries, they will also be time-aligned at the second corresponding phase boundaries. Note that if one of the two videos is an instructional/training video and the other video is a trainee video, then all video segments in the instructional/training video can be assigned with an original playback speed (i.e., used as the reference video segments during comparative playback), whereas each video segment in the trainee video is assigned with an adjusted playback speed which is computed, e.g., based on the numbers of frames in the two corresponding video segments in the two videos. Finally, process 300 outputs the two sets of individually time-aligned video segments of the two surgical videos to a comparative display system for performing a comparative learning (step 308). For example, a comparative learning session includes displaying the two sets of individually time-aligned video segments separately on two side-by-side monitors.

Comparative Learning Between a Recorded Video and a Live Video Feed

Some embodiments of this patent disclosure also provide a "teleprompter" style comparative learning technique for synchronizing/slaving the playback of a recorded video to a live video feed (or "live video"). For example, in an exemplary robotic surgery training system, the training setup can include a virtual reality (VR) environment, such as a VR headset worn by a trainee which provides the trainee with an immersive display. More specifically, when the trainee looks into the headset, the VR display screen may be split into two halves (i.e., in form of two side-by-side videos): one half (e.g., the left half) of the display may be showing a recorded training/instructional video on how to perform a surgical task, such as surgical suturing; while the other half (e.g., the right half) of the display may be showing a live video feed of the trainee performing the same surgical task by following/repeating the actions displayed in the training/instructional video.

However, a problem can arise in such a two-video comparative learning VR environment. Let's assume that the instructional video playing on the left half of the display is demonstrating suturing techniques, wherein the instructor in the video picks up a tissue with the first set of forceps, grabs a needle with the second set of forceps, and completes the first knot. Meanwhile on the right half of the display the live feed shows that the trainee is trying to replicate the same actions to tie the first knot, but has not been able to complete the first knot yet. This situation would then require the trainee to manually pause the instructional video to wait and then manually restart the instructional video again after the first knot has been completed. Without the trainee's manual intervention, the instructional video would continue to play and show the next task. However, having the trainee manually pausing and restarting the instructional video can be quite distracting for the trainee's practice, because it causes the trainee to lose focus and therefore compromises the effectiveness of the practice.

A proposed comparative learning technique between a recorded instructional video and a live video feed enables automatically pausing the instructional video to wait for the trainee/follower of the instructional video by detecting in the live video that the trainee has not finished a live task (e.g., tying the first knot by the trainee). The proposed comparative learning technique also enables automatically restarting a paused instructional video after detecting that the trainee has completed the live task. Using the proposed comparative learning technique, the trainee/follower can follow the entire procedure depicted in the instructional video without having to the manually pause and restart the instructional video.

In some embodiments, a phase segmentation engine described-above which typically operates offline on recorded videos can be applied in real-time on the trainee's live video feed. In these embodiments, if the phase segmentation engine can determine in real-time the exact task the trainee is performing, the phase segmentation engine can automatically pause or play the instructional video so that the trainee can follow the instructional video no matter at what speed the trainee is performing a current/live task. More specifically, the phase segmentation engine can be configured to segment actions depicted in the live video in real-time and determine whether a particular task is still being performed or has just been completed. Moreover, as discussed above, the phase segmentation engine can also be configured to segment the recorded instructional video offline so the phase segmentation engine has knowledge of exactly when a given task depicted in the instructional video begins and ends (i.e., the phase boundaries). Based on the segmentation information from the instructional video and the live video feed, the phase segmentation engine can then determine in real-time if the task depicted in the instructional video has ended but the task depicted in the live video is still in progress. If so, the phase segmentation engine is configured to pause the instructional video to wait for the trainee's process. Next, if the phase segmentation engine subsequently detects that the current task in the live video feed has just been completed, the phase segmentation is further configured to restart the instructional video to continue to the next task/step.

In some embodiments, to facilitate detecting the beginning and ending of each task in a given surgical procedure, a set of landmark events can be predefined. For example, if the instructional video depicts a practice of tying 5 surgical knots on a tissue, then 5 landmark events can be predefined, and each of which corresponds to the completion of each of the 5 surgical knots. Note that these predefined landmarks can be used to label or tag the instructional video so that they can be detected when the instructional video is later played back. In other words, the phase segmentation engine can be configured to detect these predefined landmarks during the instructional video playback. Hence, during practice, each time a landmark event is detected in the instructional video, the phase segmentation engine can pause the instructional video and wait for the live video feed if the corresponding landmark event in the live video has not been reached. Next, when the corresponding landmark event is also detected in the live video feed, the phase segmentation engine can restart the instructional video to demonstrate the next task.

Note that while the comparative learning technique for synchronizing a recorded video and a live video feed is described above using a simple suturing procedure comprising some simple tasks, the same technique can be applied to other recorded video and corresponding live video feed scenarios which include significantly more complex procedures. In some embodiments, when a more complex surgical procedure is being practiced, the phase segmentation engine can be configured to segment the recorded video and the live video into multiple levels of tasks of different complexities and granularities. Specifically, a more complex procedure can be segmented into a set of high-level phases of the procedure, then each of the high-level phases can be further segmented into one or more subphases, and each of the high-level phases and subphases can be further segmented into one or more simple tasks. For example, a more complex procedure can include a suturing phase followed by a stapling phase, wherein the suturing phase can further include multiple knotting tasks whereas the stapling phase can include multiple stapling tasks. Note that even a simple suturing task of tying a surgical knot can be further broken down to finer granularity, e.g., the action of picking up the thread in a suturing task can be segmented out as a subtask of the suturing task for event detection.

In some embodiments, for each level of the phases, subphases, and tasks, a corresponding set of landmark events can be predefined for event detection purposes. Hence, for a complex procedure, there can be a set of predefined landmark events for the set of high-level phases of the procedure. Within a given high-level phase, there can be a set of predefined landmark events for the set of subphases, and for each of the high-level phases or the subphases, there can be a set of predefined landmark events for the set of simple tasks. Note that all these different levels of the predefined landmark events can be used by the phase segmentation engine to pause the instructional video at any given landmark event and wait for the live video to complete the same phase/subphase/task that has just been completed in the instructional video. Note that for a sequence of predefined phases, these landmark events are similar to the phase boundaries described-above.

In some embodiments, instead of pausing and restarting the instructional video, a disclosed comparative learning technique can also slave the instructional video to the live video by controlling the playback speed and/or the frame rate of the instructional video based on the speed of action in the live video. More specifically, depending on which phase or step the trainee is currently in, the phase segmentation engine can adjust the frame rate of the video player so that the instructional video can be played at a varying speed which is slaved to the trainee's speed. In this manner, throughout the procedure, the playback speed of the instructional video continues to follow the speed of the trainee for each task the trainee is performing. Note that this playback slaving technique can be combined with the above-described pause and restart technique. In other words, at any time when the phase segmentation engine detects that the instructional video has completed a task while the same task is still ongoing in the live video, the instructional video can be automatically paused to wait for the live video to complete the same task.

Figure 4:
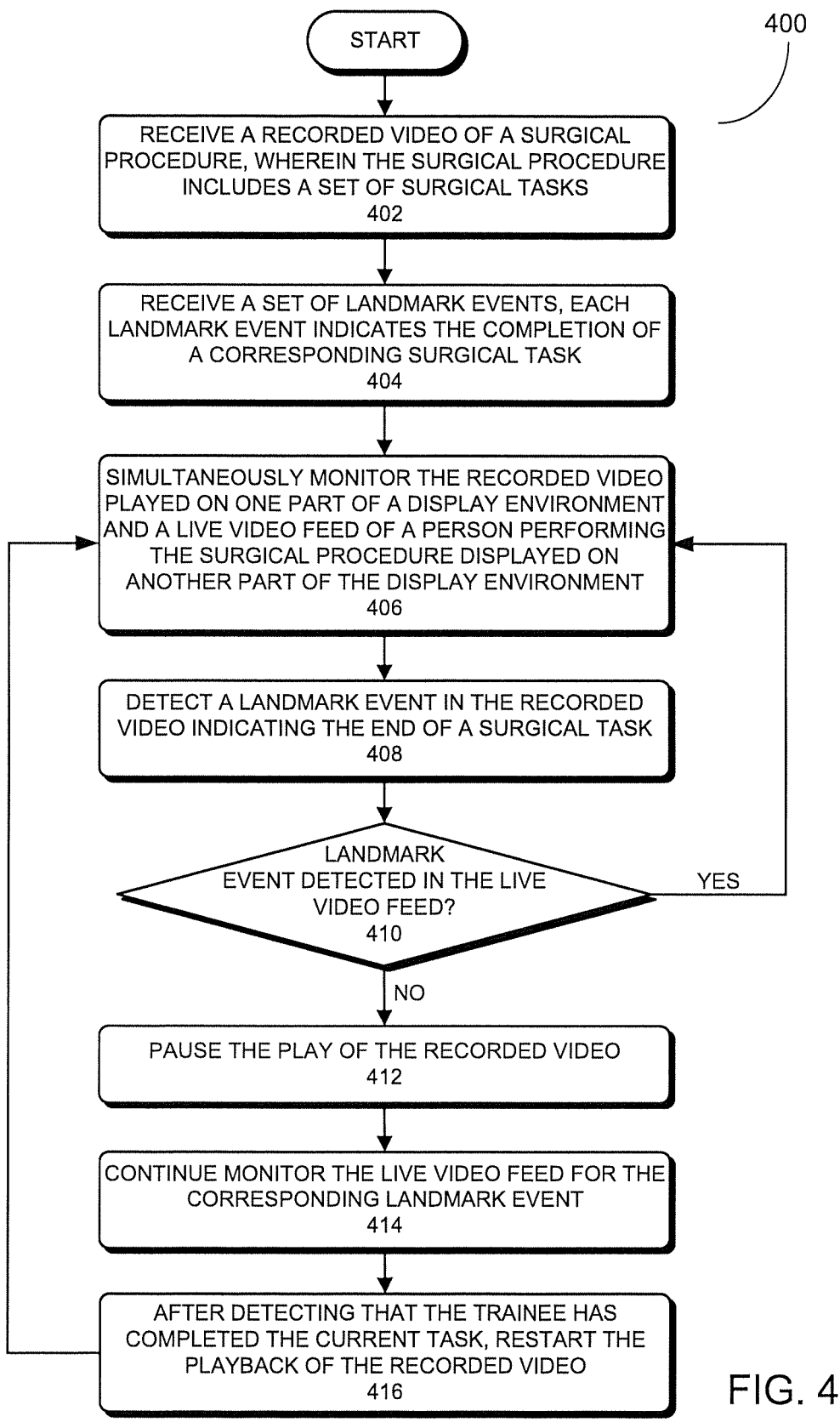
FIG. 4 presents a flowchart illustrating an exemplary process for synchronizing the playback of a recorded instructional video of a surgical procedure to a live video feed of a person replicating the same surgical procedure in accordance with some embodiments described herein.

FIG. 4 presents a flowchart illustrating an exemplary process 400 for synchronizing the playback of a recorded instructional video of a surgical procedure to a live video feed of a person replicating the same surgical procedure in accordance with some embodiments described herein. In one or more embodiments, one or more of the steps in FIG. 4 may be omitted, repeated, and/or performed in a different order. Accordingly, the specific arrangement of steps shown in FIG. 4 should not be construed as limiting the scope of the technique.

As can be seen in FIG. 4, process 400 begins by receiving a recorded video of a surgical procedure, wherein the surgical procedure includes a set of tasks (step 402). In some embodiments, the recorded video is an instructional/training video performed by an expert of the surgical procedure. Moreover, process 400 can receive a set of landmark events wherein each landmark event indicates the completion of a corresponding surgical task in the set of surgical tasks (step 404). As described above, prior to performing a comparative learning, a phase segmentation engine can be used offline to segment the recorded video into a set of video segments corresponding to the set of surgical tasks, and subsequently extract the set of landmark events. In some embodiments, each landmark event can be represented by a timestamp indicating the end/completion of a corresponding surgical task.

Next, during a live training session for performing the surgical procedure, process 400 simultaneously monitors the recorded video being played on one part of a display environment and a live video feed capturing a person (also referred to as "the follower" or "the trainee") performing the surgical procedure and being displayed on another part of the display environment (step 406). In some embodiments, the recorded video and the live video are displayed side by side. Moreover, the display environment can include a VR display environment, such as a VR headset that includes a split-screen display. In some embodiments, the trainee in the live video is trying to replicate the exact sequence of surgical tasks demonstrated in the recorded video.

Next, process 400 detects a landmark event in the recorded video indicating the end of a surgical task (step 408). For example, for a suturing task, the landmark event can include the action of cutting the thread to free the needle from a newly formed knot. In some embodiments, if the landmark event is represented by the predetermined timestamp, detecting the landmark event simply involves detecting the timestamp. Process 400 then determines if a corresponding landmark event has occurred in the live video feed (step 410), i.e., if the trainee has completed the same surgical task. Note that for the current surgical task, the trainee may complete the task faster than the demonstration of the task in the recorded video. If so, process 400 determines that the trainee has completed the current task, and subsequently returns to step 406 to continue monitoring the recorded video and the live video feed. However, if process 400 determines that the trainee has not yet completed the current task at step 410, process 400 immediately pauses the play of the recorded video (step 412), and continues monitoring the live video feed for the corresponding landmark event (step 414). After eventually detecting that the trainee has completed the current task, process 400 restarts the playback of the recorded video (step 416) and returns to step 406 to continue monitoring the playback of the remaining portion of the recorded video and the live video feed. Note that while not explicitly shown in FIG. 4, process 400 can terminate at step 408 if the detected landmark event is the last landmark event in the set of landmark events indicating that the last surgical task has been completed.

Note that by automatically pausing and restarting the recorded video based on the trainee's progress in executing each surgical task, process 400 allows the recorded video to be slaved to the live video feed by following/synchronizing to the speed of the trainee action/movement. In some embodiments, if after monitoring one or more surgical tasks, it is determined that the trainee executes the surgical tasks consistently slower than the playback of the one or more surgical tasks in the recorded video, process 400 can be configured to slow down/decrease the playback speed/frame rate of the recorded video in an amount to match the average speed of the trainee, so that the visual demonstrations in the recorded video become more synchronized to the action/movement of the trainee in the live video feed. However, if after playing one or more surgical tasks, it is determined that that the trainee executes the surgical tasks consistently faster than the playback of the one or more surgical tasks in the recorded video, process 400 can be configured to speed up/increase the playback speed/frame rate of the recorded video in an amount to match the average speed of the trainee, so that the visual demonstrations in the recorded video again become more synchronized to the action/movement of the trainee in the live video feed.

Note that while various embodiments of the present techniques are described in the scope of surgical procedure videos, the disclosed comparative-learning techniques can also be applied to other types of procedure videos other than surgical procedure videos for performing comparative learning. More specifically, for any type of procedure videos which can be broken down into a sequence of predefined and fixed number of phases/steps, the disclosed comparative-learning techniques including the disclosed phase segmentation engine and the phase synchronization engine can be used to synchronize/slave one such procedure video to another procedure video of the same type at each segmented phase/step in the sequence of phases/steps. For example, the applicable procedure videos can include non-surgical medical procedure videos and many types of know-how videos.

Figure 5:
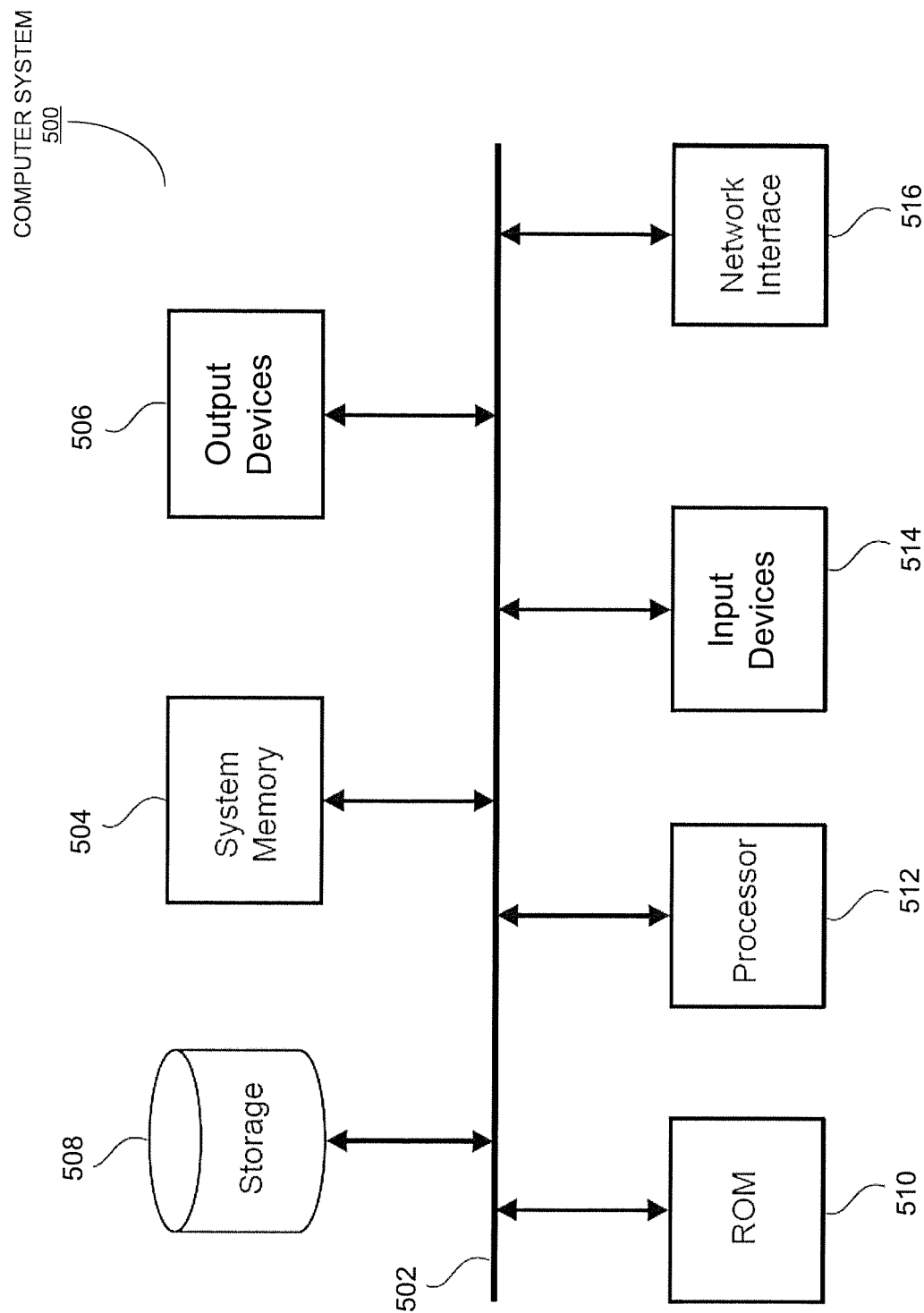
FIG. 5 conceptually illustrates a computer system with which some embodiments of the subject technology can be implemented.

FIG. 5 conceptually illustrates a computer system with which some embodiments of the subject technology can be implemented. Computer system 500 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 500 includes a bus 502, processing unit(s) 512, a system memory 504, a read-only memory (ROM) 510, a permanent storage device 508, an input device interface 514, an output device interface 506, and a network interface 516. In some embodiments, computer system 500 is a part of a robotic surgical system.

Bus 502 collectively represents all system, peripheral, and chipset buses that communicatively connect the numerous internal devices of computer system 500. For instance, bus 502 communicatively connects processing unit(s) 512 with ROM 510, system memory 504, and permanent storage device 508.

From these various memory units, processing unit(s) 512 retrieves instructions to execute and data to process in order to execute various processes described in this patent disclosure, including the disclosed process of time-synchronizing two surgical videos for comparative learning and the process of synchronizing the playback of a recorded instructional video to a live video feed in conjunction with FIGS. 1A-1B and FIGS. 2-4. The processing unit(s) 512 can include any type of processor, including, but not limited to, a microprocessor, a graphics processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 512 can be a single processor or a multi-core processor in different implementations.

ROM 510 stores static data and instructions that are needed by processing unit(s) 512 and other modules of the computer system. Permanent storage device 508, on the other hand, is a read-and-write memory device. This device is a non-volatile memory unit that stores instructions and data even when computer system 500 is off. Some implementations of the subject disclosure use a mass-storage device (such as a magnetic or optical disk and its corresponding disk drive) as permanent storage device 508.

Other implementations use a removable storage device (such as a floppy disk, flash drive, and its corresponding disk drive) as permanent storage device 508. Like permanent storage device 508, system memory 504 is a read-and-write memory device. However, unlike storage device 508, system memory 504 is a volatile read-and-write memory, such as a random access memory. System memory 504 stores some of the instructions and data that the processor needs at runtime. In some implementations, various processes described in this patent disclosure, including the disclosed process of time-synchronizing two surgical videos for comparative learning and the process of synchronizing the playback of a recorded instructional video to a live video feed in conjunction with FIGS. 1A-1B and FIGS. 2-4, are stored in system memory 504, permanent storage device 508, and/or ROM 510. From these various memory units, processing unit(s) 512 retrieve instructions to execute and data to process in order to execute the processes of some implementations.

Bus 502 also connects to input and output devices 514 and 506. Input devices 514 enable the user to communicate information to and select commands for the computer system. Input devices 514 can include, for example, alphanumeric keyboards and pointing devices (also called "cursor control devices"). Output devices 506 enable, for example, the display of images generated by computer system 500. Output devices 506 can include, for example, printers and display devices, such as cathode ray tubes (CRT) or liquid crystal displays (LCD). Some implementations include devices such as a touchscreen that functions as both input and output devices. In particular, output devices 506 can include two side-by-side monitors for simultaneously displaying two procedure videos for comparative learning.

Finally, as shown in FIG. 5, bus 502 also couples computer system 500 to a network (not shown) through a network interface 516. In this manner, the computer can be a part of a network of computers (such as a local area network ("LAN"), a wide area network ("WAN"), an intranet, or a network of networks, such as the Internet. Any or all components of computer system 500 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general-purpose processor, a digital signal processor (DSP), an application-specific integrated circuit (ASIC), a field-programmable gate array (FPGA) or other programmable-logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. Disk and disc, as used herein, include compact disc (CD), laser disc, optical disc, digital versatile disc (DVD), floppy disk, and Blu-ray disc, where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for synchronizing two surgical procedure videos, the method comprising:
    receiving a first surgical video of a surgical procedure and a second surgical video of the same surgical procedure, wherein the surgical procedure includes a sequence of predefined phases;
    performing a phase segmentation on each of the first and second surgical videos to segment the first and second surgical videos into a first set and a second set of video segments corresponding to the sequence of predefined phases;
    synchronizing each video segment in the first set of video segments corresponding to a predefined phase in the sequence of predefined phases to a corresponding video segment in the second set of video segments corresponding to the same predefined phase; and
    outputting the first and second surgical videos including the first and second sets of synchronized video segments to a display system for a comparative viewing.

2. The computer-implemented method of claim 1, wherein
    segmenting the first or the second surgical video into the first or the second set of video segments includes:
    for each phase in the sequence of predefined phases,
        identifying a first phase boundary in the first or the second surgical video representing the beginning of the phase in the first or the second surgical video;
        identifying a second phase boundary in the first or the second surgical video representing the ending of the phase in the first or the second surgical video; and
        outputting a video segment between the first phase boundary and the second phase boundary of the first or the second surgical video as the video segment corresponding to the phase,
    wherein each video segment in the first or the second set of video segments includes a corresponding set of video frames.

3. The computer-implemented method of claim 2, wherein identifying the first or the second phase boundary in the first or the second surgical video includes using a machine-learning engine to detect a surgical event in the first or the second surgical video indicative of the beginning or ending of the corresponding phase in the surgical procedure.

4. The computer-implemented method of claim 3, synchronizing each video segment in the first set of video segments of the first surgical video to a corresponding video segment in the second set of video segments of the second surgical video includes:
    time-aligning the first phase boundary of the video segment of the first surgical video to the first phase boundary of the corresponding video segment of the second surgical video; and
    determining a first playback speed for the video segment and a second playback speed for the corresponding video segment such that a first playback time of the video segment using the first playback speed is equal to or substantially equal to a second playback time of the corresponding video segment using the second playback speed, thereby causing the second phase boundary of the video segment of the first surgical video to be time-aligned to the second phase boundary of the corresponding video segment of the second surgical video.

5. The computer-implemented method of claim 1, wherein synchronizing a given video segment in the first set of video segments of the first surgical video to a corresponding video segment in the second set of video segments of the second surgical video includes:
    determining a first number of video frames contained in the given video segment;
    determining a second number of video frames contained in the corresponding video segment; and
    determining a first frame rate for playing back the given video segment and a second frame rate for playing back the corresponding video segment based on the first number and the second number of video frames, so that a first playback time of the given video segment using the first frame rate is equal to or substantially equal to a second playback time of the corresponding video segment using the second frame rate.

6. The computer-implemented method of claim 5, wherein the first frame rate is a constant frame rate for all video segments of the first surgical video, and wherein the second frame rate is computed based on the constant frame rate, and the first number and the second number of video frames.

7. The computer-implemented method of claim 1, wherein the first surgical video is a reference video, and wherein synchronizing a given video segment in the first set of video segments of the first surgical video to a corresponding video segment in the second set of video segments of the second surgical video include:
assigning a constant playback speed for all video segments in the first set of video segments; and
for each video segment in the second set of video segments, assigning an adjustable playback speed based on a playback time of the corresponding video segment in the first set of video segments when using the constant playback speed,
wherein the adjustable playback speed is configured to speed up or slow down the playback of a video segment in the second set of video segments so that the playback time of each video segment in the first set of video segments when using the constant playback speed is equal to or substantially equal to the playback time of each video segment in the second set of video segments using the adjustable playback speed.

8. The computer-implemented method of claim 1, wherein performing a comparative viewing of the first and second surgical videos includes:
outputting the first surgical video to a first monitor and the second surgical video to a second monitor which is positioned next to the first monitor; and
simultaneously starting a playback of the first surgical video on the first monitor and a playback of the second surgical video on the second monitor,
wherein playing the first surgical video and the second surgical video based on the two sets of synchronized video segments automatically synchronizes the playback of each video segment in the first set of video segments to the playback of a corresponding video segment in the second set of video segments.

9. The computer-implemented method of claim 8, wherein the playback of the first surgical video on the first monitor ends at the same time or substantially the same time as the playback of the second surgical video on the second monitor ends.

10. The computer-implemented method of claim 1, wherein performing a comparative viewing of the first and second surgical videos includes:
creating a split-screen video by combining the first and second surgical videos, wherein the corresponding video segments in the first and second surgical videos are time-aligned at the corresponding phase boundaries in the split-screen video; and
playing back the split-screen video on a monitor so that the first and second surgical videos are played side-by-side and time-aligned to each other in each of the sequence of predefined phases.

11. A system for synchronizing two surgical procedure videos, comprising:
one or more processors; and
a memory coupled to the one or more processors;
a segmentation module configured to segment a first surgical video and a second surgical video of a same surgical procedure into a first set of video segments and a second set of video segments, respectively, based on a sequence of predefined phases for the surgical procedure;
a synchronization module configured to synchronize a video segment in the first set of video segments corresponding to a predefined phase in the sequence of predefined phases to a corresponding video segment in the second set of video segments corresponding to the same predefined phase; and
an output module configured to output the synchronized video segments to a display system for a comparative viewing.

12. The system of claim 11, wherein the segmentation module is configured to segment the first surgical video or the second surgical video by:
for each phase in the sequence of predefined phases,
identifying a first phase boundary in the first or the second surgical video representing the beginning of the phase in the first or the second surgical video;
identifying a second phase boundary in the first or the second surgical video representing the ending of the phase in the first or the second surgical video; and
outputting a video segment between the first phase boundary and the second phase boundary of the first or the second surgical video as the video segment corresponding to the phase,
wherein each video segment in the first or the second set of video segments includes a corresponding set of video frames.

13. The system of claim 12, wherein the segmentation module is further configured to identify the first or the second phase boundary in the first or the second surgical video by using a machine-learning engine to detect a surgical event in the first or the second surgical video indicative of the beginning or ending of the corresponding phase in the surgical procedure.

14. The system of claim 13, wherein the synchronization module is configured to synchronize the video segment in the first set of video segments to the corresponding video segment in the second set of video segments by:
time-aligning the first phase boundary of the video segment of the first surgical video to the first phase boundary of the corresponding video segment of the second surgical video; and
determining a first playback speed for the video segment and a second playback speed for the corresponding video segment such that a first playback time of the video segment using the first playback speed is equal to or substantially equal to a second playback time of the corresponding video segment using the second playback speed, thereby causing the second phase boundary of the video segment of the first surgical video to be time-aligned to the second phase boundary of the corresponding video segment of the second surgical video.

15. The system of claim 11, wherein the synchronization module is further configured to synchronize the video segment in the first set of video segments to the corresponding video segment in the second set of video segments by:
determining a first number of video frames contained in the video segment;
determining a second number of video frames contained in the corresponding video segment; and
determining a first frame rate for playing back the video segment and a second frame rate for playing back the corresponding video segment based on the first number and the second number of video frames, so that a first playback time of the video segment using the first frame rate is equal to or substantially equal to a second playback time of the corresponding video segment using the second frame rate.

16. The system of claim 15, wherein the first frame rate is a constant frame rate for all video segments of the first surgical video, and wherein the second frame rate is computed based on the constant frame rate, and the first number and the second number of video frames.

17. The system of claim 11, wherein the first surgical video is a reference video, and wherein the synchronization module is further configured to synchronize a given video segment in the first set of video segments of the first surgical video to a corresponding video segment in the second set of video segments of the second surgical video by:
  assigning a constant playback speed for all video segments in the first set of video segments; and
  for each video segment in the second set of video segments, assigning an adjustable playback speed based on a playback time of the corresponding video segment in the first set of video segments when using the constant playback speed,
  wherein the adjustable playback speed is configured to speed up or slow down the playback of a video segment in the second set of video segments so that the playback time of each video segment in the first set of video segments when using the constant playback speed is equal to or substantially equal to the playback time of each video segment in the second set of video segments using the adjustable playback speed.

18. The system of claim 11, wherein the output module is further configured to:
  output the video segment in the first set of video segments to a first monitor and the corresponding video segment in the second set of video segments to a second monitor which is positioned next to the first monitor; and
  simultaneously start a playback of the video segment of the first surgical video on the first monitor and a playback of the corresponding video segment of the second surgical video on the second monitor,
  wherein playing the first surgical video and the second surgical video based on the two synchronized video segments automatically synchronizes the playback of the video segment of the first surgical video to the playback of the corresponding video segment of the second surgical video.

19. An apparatus for synchronizing two surgical procedure videos, comprising:
  one or more processors; and
  a memory coupled to the one or more processors;
  a segmentation module configured to segment a first surgical video and a second surgical video of a same surgical procedure into a first set of video segments and a second set of video segments, respectively, based on a sequence of predefined phases for the surgical procedure;
  a synchronization module configured to synchronize each video segment in the first set of video segments corresponding to a predefined phase in the sequence of predefined phases to a corresponding video segment in the second set of video segments corresponding to the same predefined phase; and
  an output module configured to output the first and second sets of synchronized video segments to a display system for a comparative viewing.

20. The apparatus of claim 19, wherein the first surgical video is a reference video, and wherein the synchronization module is further configured to synchronize a given video segment in the first set of video segments to a corresponding video segment in the second set of video segments by:
  assigning a constant playback speed for all video segments in the first set of video segments; and
  for each video segment in the second set of video segments, assigning an adjustable playback speed based on a playback time of the corresponding video segment in the first set of video segments when using the constant playback speed,
  wherein the adjustable playback speed is configured to speed up or slow down the playback of a video segment in the second set of video segments so that the playback time of each video segment in the first set of video segments when using the constant playback speed is equal to or substantially equal to the playback time of each video segment in the second set of video segments using the adjustable playback speed.

* * * * *